US009222102B2

(12) United States Patent
Kraus et al.

(10) Patent No.: US 9,222,102 B2
(45) Date of Patent: Dec. 29, 2015

(54) INHIBITION OF BOLTING AND FLOWERING OF A SUGAR BEET PLANT

(75) Inventors: Josef Kraus, Einbeck (DE); Andreas Menze, Goettingen (DE); David Wurbs, Einbeck (DE)

(73) Assignee: KWS SAAT SE, Einbeck (DE)

( * ) Notice: Subject to any disclaimer, the term of this patent is extended or adjusted under 35 U.S.C. 154(b) by 640 days.

(21) Appl. No.: 13/391,865

(22) PCT Filed: Sep. 15, 2010

(86) PCT No.: PCT/DE2010/001081
§ 371 (c)(1),
(2), (4) Date: Feb. 23, 2012

(87) PCT Pub. No.: WO2011/032537
PCT Pub. Date: Mar. 24, 2011

(65) Prior Publication Data
US 2012/0167247 A1    Jun. 28, 2012

(30) Foreign Application Priority Data
Sep. 15, 2009  (DE) .................. 10 2009 041 333

(51) Int. Cl.
C12N 15/82   (2006.01)
C07K 14/415  (2006.01)

(52) U.S. Cl.
CPC ............ *C12N 15/827* (2013.01); *C07K 14/415* (2013.01); *C12N 15/8218* (2013.01)

(58) Field of Classification Search
None
See application file for complete search history.

(56) References Cited

U.S. PATENT DOCUMENTS

| | | | | |
|---|---|---|---|---|
| 7,227,053 | B2 * | 6/2007 | Kanhonou et al. | 800/289 |
| 2004/0031072 | A1 * | 2/2004 | La Rosa et al. | 800/278 |
| 2006/0123505 | A1 * | 6/2006 | Kikuchi et al. | 800/278 |
| 2009/0162904 | A1 * | 6/2009 | Gielen et al. | 435/101 |
| 2009/0205073 | A1 | 8/2009 | Gielen et al. | |
| 2011/0231946 | A1 | 9/2011 | Van Roggen et al. | |

FOREIGN PATENT DOCUMENTS

| | | |
|---|---|---|
| WO | 2007122086 A1 | 11/2007 |
| WO | 2009141446 A1 | 11/2009 |
| WO | 2010025888 A2 | 3/2010 |

OTHER PUBLICATIONS

Klahre, U; et al. F.Proceedings of the National Academy of Sciences of the United States of America 99.18: 11981-11986. Natl Acad Sciences. (Sep. 3, 2002).*
Thomas, C L; et al. The Plant journal : for cell and molecular biology 25.4: 417-25. (Feb. 2001).*
Koonin, Eugene V; NLM.Annual review of genetics 39: 309-38. (2005).*
Sung Sibum et al: "A PHD finger protein involved in both the vernalization and photoperiod pathways in Arabidopsis", Genes & Development, vol. 20, No. 23, Dec. 2006, pp. 3244-3248 XP002616054, ISSN: 0890-9369 p. 3244-p. 3245; figures 1D, 1C.
Jung C et al: "Flowering time control and applications in plant breeding", Trends in Plant Science, Elsevier Science, Oxford, GB, vol. 14, No. 10, Oct. 1, 2009, pp. 563-573, XP026668259, ISSN: 1360-1385, DOI: DOI:10.1016/J.TPLANTS.2009.07.005, [retrieved on Aug. 27, 2009] p. 3; claims 29, 32, 33, 42; example 7; table 1.
Database EMBL [Online] Jan. 1, 2008, "UFL192_45 Cotton fiber 0-10 day post anthesis Gossypium hirsutum cDNA, mRNA sequence" XP002616055, retrieved from EBI accession No. EMBL:ES815074, Database accession No. ES815074, the whole document.
Database Geneseq [Online] —Oct. 18, 2007, "Glycine max cDNA Seq Id No. 128994", XP002616056, retrieved from EBI accession No. GSN:AFP37816, Database accession No. AFP37816 the whole document & US 2004/031072 AI (La Rosa•Thomas J [US] et al) Feb. 12, 2004 sequence 128994.
Database UniProt [Online] Mar. 24, 2009, "SubName: Full=Putative uncharacterized protein;", XP002616057, retrieved from EBI accession No. UNIPROT:B9RPB3 Database accession No. B9RPB3, the whole document
Bauerle, Isabel et al. "The Timing of Developmental Transitions in Plants" pp. 655-664 Department of Cell and Developmental Biology, John Innes Centre, Norwich NR4 7UH, UK Cell 125, May 19, 2006, Elsevier Inc.
Michaels, Scott D. et al. "Loss of Flowering Locus C Activity Eliminates the Late-Flowering Phenotype of Frigida and Autonomous Pathway Mutations but Not Responsiveness to Vernalization" Department of Biochemistry, University of Wisconsin The Plant Cell, vol. 13, pp. 935-941, Apr. 2001, www.plantcell.org © 2001 American Society of Plant Physiologists.
Geraldo, Nuno et al. "Frigida Delays Flowering in Arabidopsis via a Cotranscriptional Mechanism Involving Direct Interaction with the Nuclear Cap-Binding Complex" Department of Cell and Developmental Biology, John Innes Centre, Norwich NR4 7UH, United Kingdom, Plant Physiology, Jul. 2009, vol. 150, pp. 1611-1618, www.plantphysiol.org © 2009 American Society of Plant Biologists.
He, Yuehui et al. "Role of chromatin modification in flowering-time control" Department of Biochemistry, University of Wisconsin, Madison, WI www.sciencedirect.com pp. 1360-1385, © 2004 Elsevier Ltd.

(Continued)

Primary Examiner — Anne Kubelik
Assistant Examiner — Charles Logsdon
(74) Attorney, Agent, or Firm — Patent Central LLC; Stephan A. Pendorf

(57) ABSTRACT

A means for inhibiting the bolting and flowering of sugar beet plant, including an isolated nucleic acid, a vector or mobile genetic element which can be used to produce a sugar beet, in which stem elongation post-vernalization is inhibited. Further, a transgenic sugar beet plant comprising the nucleic acid, vector or mobile genetic element, in which bolting and flowering is inhibited after vernalization, a method for producing such transgenic sugar beet plant, and a process for the inhibition of bolting and flowering of sugar beet plant.

15 Claims, 8 Drawing Sheets

(56) References Cited

OTHER PUBLICATIONS

Chia, T.Y.P. et al. "Sugar beet contains a large Constans-Like gene family including a CO homologue that is independent of the early-bolting (B) gene locus" Journal of Experimental Botany, vol. 59, No. 10, pp. 2735-2748, 2008.

Reeves, Patrick A. et al. Evolutionary Conservation of the Flowering Locus C-Mediated Vernalization Response: Evidence From the Sugar Beet (Beta vulgaris) Genetics Society of America, Genetics 176: pp. 295-307 (May 2007).

Gazzani, Silvia et al. Analysis of the Molecular Basis of Flowering Time Variation in Arabidopsis Accessions1[w] Department of Cell and Development Biology, John Innes Centre, Norwich NR4 7UH, United Kingdom Plant Physiology, Jun. 2003, vol. 132, pp. 1107-1114, www.plantphysiol.org © 2003 American Society of Plant Biologists.

Boss, Paul K. et al. "Multiple Pathways in the Decision to Flower: Enabling, Promoting, and Resetting" Department of Cell and Development Biology, John Innes Centre, Norwich NR4 7UH, United Kingdom the Plant Cell, vol. 16, pp. 18-31, Supplement 2004, www.plantcell.org © 2004 American Society of Plant Biologists.

* cited by examiner

```
                    SEQUENCE LISTING

<160> NUMBER OF SEQ ID NOS: 27

<210> SEQ ID NO 1
<211> LENGTH: 2366
<212> TYPE: DNA
<213> ORGANISM: Beta vulgaris

<400> SEQUENCE: 1
atgatagaac cgcagctgaa agcatgcaac aaaaatgtga agaatccgga gagcaggaag      60
actgcttcca cttcgtacaa ttctgcttct aggaagcaaa gcaggaaggg agaaaatcct     120
attcgtgtta ctccgttagg agagcaatct tctgattttg gatgttctag tacttggata     180
tgtaaaaatt ctgcatgtag agctgttctg tctatagatg atgcgttctg tcggaggtgt     240
tcatgctgca tctgtcatca atttgatgat aataaagacc ctagtctttg gttggtttgt     300
gaatccgagt ctgggcaggg tgattcttgt ggattatcat gccatattga gtgtgcattt     360
caacaagaaa agctgggagt tgtgaacctt gggcaataca tgcatttgga tgggagttac     420
tgttgttctt cttgcggcaa agtctctggg atacttgggt cagtacttct gttttatgta     480
gtgagatatt gacctgaagt catgcttgtt ttgatgaag ataaataatt taaaaaaaat     540
gttacatgcc caactattac aaggccagta gaaaactatg agatatatta attttgatat     600
tactgtggag gctcagttga atttatatgc ttgagtttta ctcactaatg gcaggtgttg     660
gaaaaagcaa ttggctatag ctaaggatgc tcgacgtgtc gatgtgcttt gctatagaat     720
atttttgagt tacagactcc tcgagggcac agctaagttt aaggacctcc acgagattgt     780
tgcagaagct aaaacaaagc tggaggcaga ggtgggtcct atgaacggag actctgtcaa     840
gatggccaga ggtattgtta gcaggcttgc tattgctgca gatgtgcaaa agctctgttc     900
gcacgcgatt gataaagcta atgaatggct cgccaatgtt tctagcatta gttcaaattg     960
caaaggttag aatacataca gcctttattg ttctccattt acttggtgag tattctatta    1020
taataaatta ttaatttctt ttggcataat ggtggcagtg gatgcacttc ctgctgcatg    1080
caggtttcta tttgaagaag ttacttcttg ttcacttgct atagttttga tagatatccc    1140
cacaccaatg actgattccg tcaaaggcta caagctatgg tactgcaaaa gtagacatga    1200
gacttttgca agggagccta catccgtctt tccaagggag aaaagaaaaa tatctgtaaa    1260
```

| gaatctcaag ccttgcaccg agtacacatt cagaatagtt tcctacacag aagttggtga | 1320 |
| tttaggccac tctgaggcta agtgtttcac caagagtttg gagatcatta gtaagaaatc | 1380 |
| caccacagtg ggctgtaaga aggaagatcc ttgtgttgag aggagctcct cgaatgcaaa | 1440 |
| ggaacaacat aattcaaatt tggctgcaat atcttctgga ttcaaggtgc gggaccttgg | 1500 |
| gaaaatcttg cacctagcat gggcccaaga acagggttgc cttgaaggtt tctgcagtgc | 1560 |
| tgatgtagaa caatgctgtg gagtaactaa atgtgaatct ccaaaagatc accagtcacc | 1620 |
| tccacctgtt tctcgtgagc ttgacctaaa tgtagtttca gttcctgatt taaatgaaga | 1680 |
| ccttacccct cccttagagt cttcaaggga tgaagacaac ggatgcacgc tagagcgtgc | 1740 |
| tactgggcct gatgatgatg ctgcttccca tggtgttgag aagaatgggc ttgggctagc | 1800 |
| caggtcaaat ggtagtgggc caagtgatga gtctcaagct tgggctctca tccgaaatgg | 1860 |
| agatgtgcct gctgttgatt ccttggcaga gacccgtcgg aagaggtctt caagtgcgaa | 1920 |
| tgaagaaaca catgactgtg acagcactct gataaatgga tcgccatttc ggatttcagg | 1980 |
| cgggcctggt tctctagacg gtaactttga gtattgtgtg aaggtcatcc ggtggttgga | 2040 |
| gtgtgagggc tatctaaaac aggaatttag attgaaatta ttgacttggt ttagcttaag | 2100 |
| atctactgaa caagagcgtc gggtagtcag cactttcatt caaactctga tggatgatcc | 2160 |
| aaagagctta gcaggacagc tagttgattc ctttggagat ctcatatcca gcaagaggcc | 2220 |
| caggactagt ttcactagta agtttatgtc tatagttgtt ctttgattga gaaattttat | 2280 |
| gtcttctttc aaacatttct attactcttc ttattctgaa gttttggact aattttgtca | 2340 |
| tgctaattac aggcattcct tcctaa | 2366 |

<210> SEQ ID NO 2
<211> LENGTH: 2285
<212> TYPE: DNA
<213> ORGANISM: Beta vulgaris
<220> FEATURE:
<221> NAME/KEY: 3'UTR
<222> LOCATION: (1963)..(2285)

<400> SEQUENCE: 2

| atgatagaac cgcagctgaa agcatgcaac aaaaatgtga agaatccgga gagcaggaag | 60 |
| actgcttcca cttcgtacaa ttctgcttct aggaagcaaa gcaggaaggg agaaaatcct | 120 |
| attcgtgtta ctccgttagg agagcaatct tctgattttg gatgttctag tacttggata | 180 |
| tgtaaaaatt ctgcatgtag agctgttctg tctatagatg atgcgttctg tcggaggtgt | 240 |
| tcatgctgca tctgtcatca atttgatgat aataaagacc ctagtctttg gttggtttgt | 300 |
| gaatccgagt ctgggcaggg tgattcttgt ggattatcat gccatattga gtgtgcattt | 360 |
| caacaagaaa agctgggagt tgtgaacctt gggcaataca tgcatttgga tgggagttac | 420 |
| tgttgttctt cttgcggcaa agtctctggg atacttgggt gttggaaaaa gcaattggct | 480 |
| atagctaagg atgctcgacg tgtcgatgtg ctttgctata gaatatttt gagttacaga | 540 |
| ctcctcgagg gcacagctaa gtttaaggac ctccacgaga ttgttgcaga agctaaaaca | 600 |
| aagctggagg cagaggtggg tcctatgaac ggagactctg tcaagatggc cagaggtatt | 660 |
| gttagcaggc ttgctattgc tgcagatgtg caaaagctct gttcgcacgc gattgataaa | 720 |
| gctaatgaat ggctcgccaa tgtttctagc attagttcaa attgcaaagt ggatgcactt | 780 |
| cctgctgcat gcaggtttct atttgaagaa gttacttctt gttcacttgc tatagttttg | 840 |
| atagatatcc ccacaccaat gactgattcc gtcaaaggct acaagctatg gtactgcaaa | 900 |

```
agtagacatg agacttttgc aagggagcct acatccgtct ttccaaggga gaaaagaaaa      960
atatctgtaa agaatctcaa gccttgcacc gagtacacat tcagaatagt ttcctcacaca    1020 gaagttggtg atttaggcca ctctgaggct aagtgtttca ccaagagttt ggagatcatt    1080
agtaagaaat ccaccacagt gggctgtaag aaggaagatc cttgtgttga gaggagctcc    1140
tcgaatgcaa aggaacaaca taattcaaat ttggctgcaa tatcttctgg attcaaggtg    1200
cgggaccttg ggaaaatctt gcacctagca tgggcccaag aacagggttg ccttgaaggt    1260
ttctgcagtg ctgatgtaga acaatgctgt ggagtaacta aatgtgaatc tccaaaagat    1320
caccagtcac ctccacctgt ttctcgtgag cttgacctaa atgtagtttc agttcctgat    1380
ttaaatgaag accttacccc tcccttagag tcttcaaggg atgaagacaa cggatgcacg    1440
ctagagcgtg ctactgggcc tgatgatgat gctgcttccc atggtgttga aagaatggg     1500 cttgggctag ccaggtcaaa tggtagtggg ccaagtgatg agtctcaagc ttgggctctc    1560
atccgaaatg gagatgtgcc tgctgttgat tccttggcag agacccgtcg gaagaggtct    1620
tcaagtgcga atgaagaaac acatgactgt gacagcactc tgataaatgg atcgccattt    1680
cggatttcag gcgggcctgg ttctctagac ggtaactttg agtattgtgt gaaggtcatc    1740
cggtggttgg agtgtgaggg ctatctaaaa caggaattta gattgaaatt attgacttgg    1800
tttagcttaa gatctactga acaagagcgt cgggtagtca gcactttcat tcaaactctg    1860
atggatgatc caaagagctt agcaggacag ctagttgatt cctttggaga tctcatatcc    1920
agcaagaggc ccaggactag tttcactagc attccttcct aaataaatct taactaagga    1980
cggcacacat atcttggata caattcagat gtttaggaca caattttag gaggcagtac     2040 ctgattttcc tcgagaaagg gattccatca gtggttaact gcacatttta gaaggtattt    2100
gttagagttt ccttgaccac atttgtgaaa agattcacat tgagacaatc attgttgcct    2160
tctcgcattg aaggaaggat atatgcttca atgaatattt aaattctagt tcaatttact    2220
aattaattag tttgttttct caaaaaaaaa aaaaaaaaa aaaagtact agtcgacgcg      2280 tggcc                                                                2285

<210> SEQ ID NO 3
<211> LENGTH: 1499
<212> TYPE: DNA
<213> ORGANISM: Beta vulgaris

<400> SEQUENCE: 3
agaggaggaa aaaggaggaa tgactataga agaatatcta agcgatgcat tgttagatgg      60
atggatatct gttggagttg aaaactggct gtttagagca tgagtttgga agatcaaatc     120
cctacaatag gtattcaaaa atctttatta gtgtgcaaac tgcaaaggac cgcggagaaa     180
aatggaaatc ccagttatac tttgagatgg ttagaacttt tctggagaat tcctgaaatc     240
tgttccaaac tccaaagaga gcgatcaaga cttttttttt ttttttttga caaagaaaat     300
aaaaattaga atcctctctg taaggcagta tgatagaacc gcagctgaaa gcatgcaaca     360
aaaatgtgaa gaatccggag agcaggaaga ctgcttccac ttcgtacaat tctgcttcta     420
ggaagcaaag caggaaggga gaaaatccta ttcgtgttac tccgttagga gagcaatctt     480
ctgattttgg atgttctagt acttggatat gtaaaaattc tgcatgtaga gctgttctgt     540
ctatagatga tgcgttctgt cggaggtgtt catgctgcat ctgtcatcaa tttgatgata     600
ataaagaccc tagtctttgg ttggtttgtg aatccgagtc tgggcagggt gattcttgtg     660
gattatcatg ccatattgag tgtgcatttc aacaagaaaa gctgggagtt gtgaaccttg     720
```

```
ggcaatacat gcatttggat gggagttact gttgttcttc tgcggcaaa gtctctggga      780 tacttgggtg ttggaaaaag caattggcta tagctaagga tgctcgacgt gtcgatgtgc      840
tttgctatag aatattttg agttacagac tcctcgaggg cacagctaag tttaaggacc      900
tccacgagat tgttgcagaa gctaaaacaa agctggaggc agaggtgggt cctatgaacg      960
gagactctgt caagatggcc agaggtattg ttagcaggct tgctattgct gcagatgtgc     1020
aaaagctctg ttcgcacgcg attgataaag ctaatgaatg gctcgccaat gtttctagca     1080
ttagttcaaa ttgcaaagtg gatgcacttc ctgctgcatg caggtttcta tttgaagaag     1140
ttacttcttg ttcacttgct atagttttga tagatatccc cacaccaatg actgattccg     1200
tcaaaggcta caagctatgg tactgcaaaa gtagacatga gacttttgca agggagccta     1260
catccgtctt tccaagggag aaaagaaaaa tatctgtaaa gaatctcaag ccttgcaccg     1320
agtacacatt cagaatagtt tcctacacag aagttggtga tttaggccac tctgaggcta     1380
agtgtttcac caagagtttg gagatcatta gtaagaaatc caccacagtg ggctgtaaaa     1440
aggaagatcc ttgtgttgag aggagctcct cgaatgcaag agaacacata attcaaatt      1499
```

<210> SEQ ID NO 4
<211> LENGTH: 653
<212> TYPE: PRT
<213> ORGANISM: Beta vulgaris

<400> SEQUENCE: 4

```
Met Ile Glu Pro Gln Leu Lys Ala Cys Asn Lys Asn Val Lys Asn Pro
1               5                   10                  15

Glu Ser Arg Lys Thr Ala Ser Thr Ser Tyr Asn Ser Ala Ser Arg Lys
            20                  25                  30

Gln Ser Arg Lys Gly Glu Asn Pro Ile Arg Val Thr Pro Leu Gly Glu
        35                  40                  45

Gln Ser Ser Asp Phe Gly Cys Ser Ser Thr Trp Ile Cys Lys Asn Ser
    50                  55                  60

Ala Cys Arg Ala Val Leu Ser Ile Asp Asp Ala Phe Cys Arg Arg Cys
65                  70                  75                  80

Ser Cys Cys Ile Cys His Gln Phe Asp Asp Asn Lys Asp Pro Ser Leu
                85                  90                  95

Trp Leu Val Cys Glu Ser Glu Ser Gly Gln Gly Asp Ser Cys Gly Leu
            100                 105                 110

Ser Cys His Ile Glu Cys Ala Phe Gln Gln Glu Lys Leu Gly Val Val
        115                 120                 125

Asn Leu Gly Gln Tyr Met His Leu Asp Gly Ser Tyr Cys Cys Ser Ser
    130                 135                 140

Cys Gly Lys Val Ser Gly Ile Leu Gly Cys Trp Lys Lys Gln Leu Ala
145                 150                 155                 160

Ile Ala Lys Asp Ala Arg Arg Val Asp Val Leu Cys Tyr Arg Ile Phe
                165                 170                 175

Leu Ser Tyr Arg Leu Leu Glu Gly Thr Ala Lys Phe Lys Asp Leu His
            180                 185                 190

Glu Ile Val Ala Glu Ala Lys Thr Lys Leu Glu Ala Glu Val Gly Pro
        195                 200                 205

Met Asn Gly Asp Ser Val Lys Met Ala Arg Gly Ile Val Ser Arg Leu
    210                 215                 220

Ala Ile Ala Ala Asp Val Gln Lys Leu Cys Ser His Ala Ile Asp Lys
225                 230                 235                 240
```

-continued

```
Ala Asn Glu Trp Leu Ala Asn Val Ser Ser Ile Ser Asn Cys Lys
            245             250             255

Val Asp Ala Leu Pro Ala Ala Cys Arg Phe Leu Phe Glu Glu Val Thr
        260             265             270

Ser Cys Ser Leu Ala Ile Val Leu Ile Asp Ile Pro Thr Pro Met Thr
        275             280             285

Asp Ser Val Lys Gly Tyr Lys Leu Trp Tyr Cys Lys Ser Arg His Glu
        290             295             300

Thr Phe Ala Arg Glu Pro Thr Ser Val Phe Pro Arg Glu Lys Arg Lys
305             310             315             320

Ile Ser Val Lys Asn Leu Lys Pro Cys Thr Glu Tyr Thr Phe Arg Ile
                325             330             335

Val Ser Tyr Thr Glu Val Gly Asp Leu Gly His Ser Glu Ala Lys Cys
            340             345             350

Phe Thr Lys Ser Leu Glu Ile Ile Ser Lys Lys Ser Thr Thr Val Gly
        355             360             365

Cys Lys Lys Glu Asp Pro Cys Val Glu Arg Ser Ser Asn Ala Lys
        370             375             380

Glu Gln His Asn Ser Asn Leu Ala Ala Ile Ser Ser Gly Phe Lys Val
385             390             395             400

Arg Asp Leu Gly Lys Ile Leu His Leu Ala Trp Ala Gln Glu Gln Gly
                405             410             415

Cys Leu Glu Gly Phe Cys Ser Ala Asp Val Gln Cys Cys Gly Val
            420             425             430

Thr Lys Cys Glu Ser Pro Lys Asp His Gln Ser Pro Pro Val Ser
        435             440             445

Arg Glu Leu Asp Leu Asn Val Val Ser Val Pro Asp Leu Asn Glu Asp
        450             455             460

Leu Thr Pro Pro Leu Glu Ser Ser Arg Asp Glu Asp Asn Gly Cys Thr
465             470             475             480

Leu Glu Arg Ala Thr Gly Pro Asp Asp Ala Ala Ser His Gly Val
                485             490             495

Glu Lys Asn Gly Leu Gly Leu Ala Arg Ser Asn Gly Ser Gly Pro Ser
            500             505             510

Asp Glu Ser Gln Ala Trp Ala Leu Ile Arg Asn Gly Asp Val Pro Ala
        515             520             525

Val Asp Ser Leu Ala Glu Thr Arg Arg Lys Arg Ser Ser Ala Asn
        530             535             540

Glu Glu Thr His Asp Cys Asp Ser Thr Leu Ile Asn Gly Ser Pro Phe
545             550             555             560

Arg Ile Ser Gly Gly Pro Gly Ser Leu Asp Gly Asn Phe Glu Tyr Cys
                565             570             575

Val Lys Val Ile Arg Trp Leu Glu Cys Glu Gly Tyr Leu Lys Gln Glu
            580             585             590

Phe Arg Leu Lys Leu Leu Thr Trp Phe Ser Leu Arg Ser Thr Glu Gln
        595             600             605

Glu Arg Arg Val Val Ser Thr Phe Ile Gln Thr Leu Met Asp Asp Pro
610             615             620

Lys Ser Leu Ala Gly Gln Leu Val Asp Ser Phe Gly Asp Leu Ile Ser
625             630             635             640

Ser Lys Arg Pro Arg Thr Ser Phe Thr Ser Ile Pro Ser
                645             650
```

```
<210> SEQ ID NO 5
<211> LENGTH: 303
<212> TYPE: DNA
<213> ORGANISM: Beta vulgaris

<400> SEQUENCE: 5
ctgggatact tgggtgttgg aaaaagcaat tggctatagc taaggatgct cgacgtgtcg      60
atgtgctttg ctatagaata tttttgagtt acagactcct cgagggcaca gctaagttta     120
aggacctcca cgagattgtt gcagaagcta aacaaagct ggaggcagag gtgggtccta      180
tgaacggaga ctctgtcaag atggccagag gtattgttag caggcttgct attgctgcag     240
atgtgcaaaa gctctgttcg cacgcgattg ataaagctaa tgaatggctc gccaatgttt     300
cta                                                                   303

<210> SEQ ID NO 6
<211> LENGTH: 419
<212> TYPE: DNA
<213> ORGANISM: Beta vulgaris

<400> SEQUENCE: 6
gatacttggg tgttggaaaa agcaattggc tatagctaag gatgctcgac gtgtcgatgt      60
gctttgctat agaatatttt tgagttacag actcctcgag ggcacagcta agtttaagga     120
cctccacgag attgttgcag aagctaaaac aaagctggag gcagaggtgg gtcctatgaa     180
cggagactct gtcaagatgg ccagaggtat tgttagcagg cttgctattg ctgcagatgt     240
gcaaaagctc tgttcgcacg cgattgataa agctaatgaa tggctcgcca atgtttctag     300
cattagttca aattgcaaag tggatgcact tcctgctgca tgcaggtttc tatttgaaga     360
agttacttct tgttcacttg ctatagtttt gatagatatc cccacaccaa tgactgatt      419

<210> SEQ ID NO 7
<211> LENGTH: 476
<212> TYPE: DNA
<213> ORGANISM: Beta vulgaris

<400> SEQUENCE: 7
caagatggcc agaggtattg ttagcaggct tgctattgct gcagatgtgc aaaagctctg      60
ttcgcacgcg attgataaag ctaatgaatg gctcgccaat gtttctagca ttagttcaaa     120
ttgcaaagtg gatgcacttc ctgctgcatg caggtttcta tttgaagaag ttacttcttg     180
ttcacttgct atagttttga tagatatccc cacaccaatg actgattccg tcaaaggcta     240
caagctatgg tactgcaaaa gtagacatga acttttgca agggagccta catccgtctt     300
tccaagggag aaaagaaaaa tatctgtaaa gaatctcaag ccttgcaccg agtacacatt     360
cagaatagtt tcctacacag aagttggtga tttaggccac tctgaggcta agtgtttcac     420
caagagtttg gagatcatta gtaagaaatc caccacagtg ggctgtaaaa aggaag        476

<210> SEQ ID NO 8
<211> LENGTH: 27
<212> TYPE: DNA
<213> ORGANISM: Artificial Sequence
<220> FEATURE:
<223> OTHER INFORMATION: Primer

<400> SEQUENCE: 8
ctgggatact tgggtgttgg aaaaagc                                          27
```

<210> SEQ ID NO 9
<211> LENGTH: 28
<212> TYPE: DNA
<213> ORGANISM: Artificial Sequence
<220> FEATURE:
<223> OTHER INFORMATION: Primer

<400> SEQUENCE: 9
tagaaacatt ggcgagccat tcattagc                                28

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
gatacttggg tgttggaaaa agca                                    24

<210> SEQ ID NO 11
<211> LENGTH: 23
<212> TYPE: DNA
<213> ORGANISM: Artificial Sequence
<220> FEATURE:
<223> OTHER INFORMATION: Primer

<400> SEQUENCE: 11
aatcagtcat tggtgtgggg ata                                     23

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
caagatggcc agaggtattg t                                       21

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
cttccttttt acagcccact g                                       21

<210> SEQ ID NO 14
<211> LENGTH: 30
<212> TYPE: DNA
<213> ORGANISM: Artificial Sequence
<220> FEATURE:
<223> OTHER INFORMATION: Primer

<400> SEQUENCE: 14
gagaggacgt cgacctggga tacttgggtg                              30

<210> SEQ ID NO 15
<211> LENGTH: 26
<212> TYPE: DNA
<213> ORGANISM: Artificial Sequence
<220> FEATURE:
<223> OTHER INFORMATION: Primer -continued

<400> SEQUENCE: 15 cccccccgggt agaaacattg gcgagc                                          26

<210> SEQ ID NO 16
<211> LENGTH: 30
<212> TYPE: DNA
<213> ORGANISM: Artificial Sequence
<220> FEATURE:
<223> OTHER INFORMATION: Primer

<400> SEQUENCE: 16
gagaggacgt cgacgatact tgggtgttgg                                       30

<210> SEQ ID NO 17
<211> LENGTH: 32
<212> TYPE: DNA
<213> ORGANISM: Artificial Sequence
<220> FEATURE:
<223> OTHER INFORMATION: Primer

<400> SEQUENCE: 17 cccccccggga atcagtcatt ggtgtgggga ta                                   32

<210> SEQ ID NO 18
<211> LENGTH: 30
<212> TYPE: DNA
<213> ORGANISM: Artificial Sequence
<220> FEATURE:
<223> OTHER INFORMATION: Primer

<400> SEQUENCE: 18
gagaggacct cgagcaagat ggccagaggt                                       30

<210> SEQ ID NO 19
<211> LENGTH: 25
<212> TYPE: DNA
<213> ORGANISM: Artificial Sequence
<220> FEATURE:
<223> OTHER INFORMATION: Primer

<400> SEQUENCE: 19
gtcgaccccc ccgggcttcc ttttt                                            25

<210> SEQ ID NO 20
<211> LENGTH: 19
<212> TYPE: DNA
<213> ORGANISM: Artificial Sequence
<220> FEATURE:
<223> OTHER INFORMATION: Primer

<400> SEQUENCE: 20
gtggagaggc tattcggta                                                   19

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
ccaccatgat attcggcaag                                                  20

```
<210> SEQ ID NO 22
<211> LENGTH: 24
<212> TYPE: DNA
<213> ORGANISM: Artificial Sequence
<220> FEATURE:
<223> OTHER INFORMATION: Primer

<400> SEQUENCE: 22
tgacctaaat gtagtttcag ttcc                                              24

<210> SEQ ID NO 23
<211> LENGTH: 23
<212> TYPE: DNA
<213> ORGANISM: Artificial Sequence
<220> FEATURE:
<223> OTHER INFORMATION: Primer

<400> SEQUENCE: 23
tcaaagttac cgtctagaga acc                                               23

<210> SEQ ID NO 24
<211> LENGTH: 24
<212> TYPE: DNA
<213> ORGANISM: Artificial Sequence
<220> FEATURE:
<223> OTHER INFORMATION: Primer

<400> SEQUENCE: 24
gaggaactag acatggggat acat                                              24

<210> SEQ ID NO 25
<211> LENGTH: 26
<212> TYPE: DNA
<213> ORGANISM: Artificial Sequence
<220> FEATURE:
<223> OTHER INFORMATION: Primer

<400> SEQUENCE: 25
gcgatacaaa gtagacatta gaactc                                            26

<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
taggaagcaa agcaggaagg ga                                                22

<210> SEQ ID NO 27
<211> LENGTH: 22
<212> TYPE: DNA
<213> ORGANISM: Artificial Sequence
<220> FEATURE:
<223> OTHER INFORMATION: Primer

<400> SEQUENCE: 27
cctccgacag aacgcatcat ct                                                22
```

INHIBITION OF BOLTING AND FLOWERING OF A SUGAR BEET PLANT

The present invention relates to an isolated nucleic acid for inhibiting bolting and flowering of a sugar beet plant, as well as the use thereof, a protein, a method for producing a transgenic sugar beet plant in which the seed stalk formation and flowering is inhibited after vernalization, vectors or mobile genetic elements, as well as a transgenic sugar beet in which the bolting and flowering is inhibited after vernalization, and seeds as well as their parts.

It is possible to use molecular biological techniques to genetically modify crops in order to change their properties and thus to improve them. One property of importance in the cultivation and use of biennial plants such as sugar beet (*Beta vulgaris*) is that the bolting and subsequent flowering requires an induction by a longer period of cold weather, as regularly occurs in temperate latitudes in winter. This transition from the vegetative to the generative phase induced by a prolonged period of low temperature is referred to as vernalization.

There are several metabolic pathways by which flowering is controlled. These include inter alia the photoperiodic metabolic pathway, an autonomous, a gibberellic acid and vernalization dependent pathway. A large number of genes involved in the regulation of flowering have been identified in recent years. In particular the control of the timing of flowering was extensively explored in the model plant *Arabidopsis* (Boss, P K, Bastow R M, Mylne, J S, and Dean, C. (2004) Multiple pathways in the decision to flower: enabling, promoting, and resetting, Plant Cell 16 Suppl: 18-31; He, Y. and Amasino, R M (2005) Role of chromatin modification in flowering-time control, Trends Plant Sci 10, 30-35; Baurle, I. and Dean, C. (2006) The timing of developmental transitions in plants, *Cell,* 125 (4): 655-664). Primarily using *Arabidopsis* mutants many "early flowering" or "late-flowering" genes were identified (Gazzani S., Gendall, A R, Lister, C., and Dean, C. (2003) Analysis of the molecular basis of flowering time variation in *Arabidopsis* accessions, Plant Physiol 132: 1107-1114; Geraldo, N., Baurle, I., Kidou, S., Hu, X., and Dean, C. (2009), FRIGIDA Delays Flowering in *Arabidopsis* via a Mechanism Involving Cotranscriptional Direct Interaction with the Nuclear Cap-Binding Complex, Plant Physiology, Jul. 1, 2009; 150 (3): 1611-1618, Michaels S D, Amasino, R M (2001) Loss of FLOWERING LOCUS C activity eliminates the late-flowering phenotype of FRIGIDA and autonomous pathway mutations but not responsiveness to vernalization, Plant Cell 13: 935-942).

In sugar beet so far only BvFLC has been characterized in detail. Therein it has been shown that this gene is not a key control gene for flowering or vernalization in sugar beet (Reeves, P A, He Y, Schmitz R J, Amasino R M, Panella, L W, Richards C M (2007), Evolutionary FLOWERING LOCUS conservation of the C-mediated vernalization response: evidence from the sugar beet (*Beta vulgaris*), Genetics 176 (1): 295-307; Chia, T. Y. P., Müller, A., Young, C., and Mutasa-Göttgens, E. S. (2008), Sugar beet contains a large CONSTANS-LIKE gene family including a CO homologue that is independent of the early-bolting (B) gene locus, J Exp Bot 59 (10): 2735-2748).

Bolting and flowering of sugar beet plants is undesirable, since in the case of sugar beets it is not the seeds or fruits, but rather the underground part of the plant, the storage root, that is used, and the energy stored in the root would be consumed during the bolting and flowering of the plant. Moreover, in some plants, which are called "bolters", an unwanted emergence of shoots occurs in the first year of growing, which is very disadvantageous in harvesting and processing.

It is thus the object of the present invention to provide means to make it possible to inhibit bolting and/or flowering of sugar beets, and even to completely prevent this.

According to the invention the problem is solved by means of an isolated nucleic acid, wherein the nucleic acid comprises a nucleotide sequence which a) exhibits a sequence or partial sequence of SEQ ID NO: 1-3, or b) is complementary to a sequence or partial sequence of SEQ ID NO: 1-3, or c) exhibits in the antisense direction a sequence or partial sequence of SEQ ID NO: 1-3 or a complementary sequence thereof, or d) is a homolog to a sequence or partial sequence of SEQ ID NO: 1-3, or e) is at least 80% identical to a sequence or partial sequence of SEQ ID NO: 1-3, or f) encodes a protein or a part of the protein with the amino acid sequence of SEQ ID NO: 4, or g) encodes a protein with an amino acid sequence of *Beta vulgaris* which is a homolog to the sequence of SEQ ID NO: 4 or a partial sequence of SEQ ID NO: 4, or h) hybridizes under stringent conditions with a sequence or partial sequence of SEQ ID NO: 1-3 or a nucleotide sequence complementary thereto or a nucleotide sequence oriented in the antisense direction thereto.

The inventive nucleic acid can be used, for example by the RNAi approach or miRNA interference approach (Fire, A, Xu, S, Montgomery, M, Kostas, S, Driver, S, Mello, C. (1998). Potent and specific genetic interference by double-stranded RNA in *Caenorhabditis elegans*, Nature 391 (6669): 806-811) to inhibit bolting and flowering of sugar beet, and in particular, if possible, to completely prevent bolting and flowering, for example by inhibiting genes that encoded flowering inducers such as FT, FUL, Co, or VIN3.

The nucleic acid is characterized especially by the fact that transgenic plants, in particular sugar beets, with special characteristics can be produced with it: In beneficial manner they can be used for example for the following purposes or with the following benefits:

Production of non-bolting, non-flowering sugar beet
Production of a sugar beet as winter beet
Production of a sugar beet as spring beet
Increasing the biomass of the sugar beet
Increasing the sugar yield
Avoiding sugar beet bolters
Extension of the sugar beet campaign
Avoidance of losses in sugar beet storage material
Utilization of the higher humidity in the fall
Covering of soil and use of the stored nitrogen
Protection for beneficial insects in the field Sugar beet is a biennial plant. After completion of the winter, and the vernalization resulting therefrom, the sugar beet usually blooms in the second year. By means of the inventive nucleic acid, for example, a sequence shown in SEQ ID NO: 5 and SEQ ID NO: 7 or another novel sequence or partial sequence inserted using an RNAi or microRNA-approach, genes can be inhibited and the effects of vernalization can be inhibited or completely prevented. Mechanisms and methods for inhibiting or switching off genes are known to the person of ordinary skill in the art, for example, under the term "gene silencing" and include the already mentioned and known to those skilled in the art of RNAi or micro (mi) RNA processes, but are not limited thereto. In an RNAi approach, for example, the sequences of SEQ ID NO: 5 to SEQ ID NO: 7 can, by molecular biology techniques known in the art of, be introduced into a sugar beet cell in the antisense orientation and under control of a suitable promoter be expressed there.

In accordance with the present invention, the bolting and flowering of the plant can be completely suppressed. The beet seed can be sown sooner, which ultimately leads to a longer growing season and thus leads to a higher biomass and a higher sugar yield. In combination with cold tolerance, the beets can, for example, be grown as so-called winter beets. In the case of planting of the beet sugars in August, in the following spring they can already be harvested as spring beets. This allows the farmer an additional crop rotation. By using the nucleic acid according to the invention, even in the case of prolonged cold spells on the field after sowing, there is no longer increased formation of bolters. Even the normal sugar beet bolters previously observed without prolonged cold spells can be prevented or at least significantly reduced. Using the present invention it can not only be accomplished that bolting and the subsequent flowering of sugar beet after an initial vernalization, but, i.e. in the second year, is inhibited or prevented, but the sugar beet can also be subjected to other cold periods without vernalization effects observed.

The sugar beet cultivation is usually from April to October/November. Since not harvested sugar beet all can be processed at the same time, they must be stored or intermediate stored. During storage, for example in piles, large losses in storage substance (sucrose losses) occur as a result of by cleavage of sucrose into glucose and fructose. By means of the inventive nucleic acid, particularly when used in an RNAi approach, the sowing and harvest dates can be varied so that the total harvest (campaign) can be extended without loss of harvest. It can allow more sugar beets to be processed for a prolonged period with less loss of storage material.

The term "sugar beet" or "sugar beet plant" is understood to refer to a plant of the genus *Beta vulgaris*, e.g. *Beta vulgaris* ssp. *vulgaris* var *altissima* (sugar beet in the narrow sense), *Beta vulgaris* ssp. *maritima* (sea beet), *Beta vulgaris* ssp. *vulgaris* var *vulgaris* (Mangold beet), *Beta vulgaris* ssp. *vulgaris* var *conditiva* (red beetroot/beet), *Beta vulgaris* ssp. *crassa vulgaris* var/alba (fodder beet).

An "isolated nucleic acid" is understood to be a nucleic acid isolated from its natural or original environment. The term also includes a synthetic manufactured nucleic acid.

An "inhibition of bolting and flowering" of a sugar beet plant refers to a reduction in the proportion of bolting and possibly flower forming sugar beet plants in comparison to a non-inventively modified sugar beet plant in a comparable stage of development, particularly in the second year after passing through a corresponding cold period, i.e. after vernalization. In particular, the concept encompasses a reduction of proportion of bolters so as to not exceed 80%, preferably at most 70%, 60%, 50%, 40%, 30%, 20% or 10%, more preferably at most 5%, 4%, 3%, 2%, 1%, 0.5%, 0.4%, 0.3%, 0.2% or 0.1% of the percentage of bolting compared to control plants not according to the invention. "Control plants" are preferably plants of the same variety, but they are not changed according to the present invention, and exhibit for example a proportion of bolters of at most 0.01%. The term "suppression" or "complete suppression" of bolting and flowering is understood to mean inhibition of at least 99%, preferably at least 99.5%, more preferably at least 99.8%, or at least 99.9%, that is, a reduction of the bolters share to at most 1%, maximum 0.5%, maximum 0.2% or at most 0.1%, especially in the second year after vernalization, compared to a non-inventively modified sugar beet plant, for example, a bolting percentage of maximal 0.01%. The concept of inhibition or suppression of bolting and flowering comprises mainly the inhibition/suppression of shoot formation, regardless of whether it comes to a flowering of the plant or not.

The term "transgenic" here means genetically modified. The term includes, when used herein, also the case that a species-specific nucleic acid in a form, arrangement or quantity is introduced into the cell where the nucleic acid does not occur naturally in the cell.

The term "homology" refers to analogies or similarities in the nucleotide sequence of two nucleic acid molecules or the amino acid sequence of two proteins or peptides. The presence of homology between two nucleic acids or proteins can be detected by comparing one position in one sequence with the corresponding position in the other sequence and determining whether identical or similar residues are present here. Two compared sequences are homologous if there is a minimum level of identical or similar nucleotides. "Identical" means that when comparing two sequences at equivalent points in each case there is the same nucleotide or the same amino acid. It may be necessary to take into account gaps in sequence to produce the best possible alignment comparison of sequences. Similar nucleotides/amino acids are non-identical nucleotides/amino acids with the same or equivalent physical and chemical properties. Exchanging a nucleotide (an amino acid) with a different nucleotide (another amino acid) with the same or equivalent physical and chemical properties is called a "conservative exchange." Examples of physico-chemical properties of an amino acid include, for example, the hydrophobicity or charge. In the context of nucleic acids there is also understood a conservative or a similar nucleotide exchange when replacing a nucleotide in a coding sequence in a codon by another, but, due to the degeneration of the genetic code, the same amino acid or a similar amino acid sequence as in the comparison of the codon affected by the exchange is encoded. The skilled worker knows which nucleotide or amino acid exchange is a conservative exchange. To determine the degree of similarity or identity between two nucleic acids, a minimum length of 60 nucleotides or base pairs is assumed, preferably a minimum length of 70, 80, 90, 100, 110, 120, 140, 160, 180, 200, 250, 300, 350 or 400 nucleotides or base pairs, more preferably the full length of the compared nucleic acids, and in the case of proteins/peptides a minimum length of 20 amino acids is assumed, preferably a minimum length of 25, 30, 35, 40, 45, 50, 60, 80, 100, 150, 200, 250 or 300 amino acids, and particularly preferably the full length of the compared amino acid sequences. The degree of similarity ("positives") or identity of two sequences can be determined using, for example, the computer program BLAST™ (Altschul S. F. et al (1990), Basic Local Alignment Search Tool, J. Mol Biol 215: 403-410; see e.g. www.ncbi.nlm.nih.gov) using standard parameters. The determination of homology depends on the length of the compared sequences. For the purposes of the present invention a homology between two nucleic acid sequences, whose shorter one's length is at least 100 nucleotides, is established if at least 70%, at least 75%, at least 80%, at least 85%, at least 90%, at least 95%, at least 97%, at least 98%, or at least 99% of nucleotides are identical and/or similar ("identities" or "positives" according to BLAST™), and preferably are identical. In the case of a sequence length of 50-99 nucleotides a homology between sequences is understood where there is identity or similarity of at least 80%, preferably at least 85%, 86%, 87%, 88% or 89%, with a sequence length of 15-49 nucleotides with an identity or similarity of at least 90%, preferably at least 95%, 96%, 97%, 98% or 99%. In the case of proteins a homology is assumed, when using the computer program BLAST™ using standard parameters and the BLOSUM62 substitution matrix (Henikoff, S., and Henikoff, J., Amino acid substitution matrices from protein blocks. Proc. Natl. Acad. Sci. USA 89: 10915-10919, 1992) an identity ("identities") and/or likeness ("positive"), preferably identity, at least 25%, at least 26%, at least 27%, at least 28%, at least 29% at least 30%, preferably at least 35%, at least 40%, at least 45%, at least 50%, at least 55%, at least 60%, at least 65%, at least 70%, at least 75%, at least 80%, at least 85%, at least 90%, at least 95%, at least 97%, at least 98%, or at least 99% is obtained, preferably the entire length of the protein/peptide, which is compared with another protein, e.g. the length of 653 amino acids in the case of SEQ ID NO: 4. The person working in this art is able with his expert knowledge to use readily available BLAST™ programs (e.g. BLASTn, BLASTp, BLASTx, tBLASTn or tBLASTx) to determine the homology in question. In addition, there are other programs that the expert knows, and which he can use in the case in assessing the homology of two or more comparative sequences or partial sequences. Such programs include those that can be found, for example on the website of the European Bioinformatics Institute (EMBL) (see, eg www.e-bi.ac.uk)

The term "hybridizing" or "hybridization" means a process in which a single-stranded nucleic acid molecule attaches itself to a complementary nucleic acid strand, i.e. agrees with this base pairing. Standard procedures for hybridization are described, for example, in Sambrook et al. (Molecular Cloning. A Laboratory Manual, Cold Spring Harbor Laboratory Press, 3rd edition 2001). Preferably this will be understood that at least 50%, more preferably at least 55%, 60%, 65%, 70%, 75%, 80% or 85%, more preferably 90%, 91%, 92%, 93%, 94% received 95%, 96%, 97%, 98% or 99% of the bases of the nucleic acid strand shows a base pairing with the complementary nucleic acid strand. The possibility of such attachment depends on the stringency of the hybridization conditions. The term "stringency" refers to hybridization conditions. High stringency is when base pairing is more difficult, low stringency, when a base-pairing is facilitated. The stringency of hybridization conditions depends for example on the salt concentration or ionic strength and temperature. Generally, the stringency can be increased by increasing the temperature and/or decreasing salinity. "Stringent hybridization conditions" are defined as conditions in which hybridization occurs predominantly only between homologous nucleic acid molecules. The term "hybridization conditions" refers not only to the actual attachment of the nucleic acids at the prevailing conditions, but also in the subsequent washing steps prevailing conditions. Stringent hybridization conditions are, for example, conditions under which predominantly only those nucleic acid molecules having at least 70%, preferably at least 75%, at least 80%, at least 85%, at least 90% or at least 95% sequence identity hybridize. Less stringent hybridization conditions include: hybridization in 4×SSC at 37° C., followed by repeated washing in 1×SSC at room temperature. Stringent hybridization conditions include: hybridization in 4×SSC at 65° C., followed by repeated washing in 0.1×SSC at 65° C. for a total of about 1 hour.

The term "complementary" refers to the ability of purine and pyrimidine nucleotides to form base pairs with each other via bridging hydrogen bonds. Complementary base pairs are, for example, guanine and cytosine, adenine and thymine and adenine and uracil. A complementary nucleic acid strand is accordingly a nucleic acid strand that can, by pairing with complementary bases of another nucleic acid strand, form a double strand.

A "fragment" or a "partial sequence" of a nucleic acid is here understood to be a contiguous section of the nucleic acid, i.e. a sequence segment of consecutive nucleotides of the nucleic acid. Fragments can e.g. be used advantageously in an RNAi or miRNA approach, where the sequence can be used, for example, in anti-sense ("antisense") direction. "Antisense direction" or "antisense orientation" of a nucleic acid sequence, e.g. a DNA sequence, means here, for example, that a transcription of the DNA sequence results in an mRNA whose nucleotide sequence is complementary to a natural (endogenous) mRNA, so that their translation is hindered or prevented by the attachment of the complementary RNA. An "antisense RNA" or "antisense RNA" is understood to mean one of a particular mRNA or other RNAs complementary to specific RNA. "Anti-sense direction" or "antisense orientation" of an mRNA sequence, therefore, means that the mRNA has a sequence that is complementary to an mRNA sequence, so that its translation may be hindered or prevented by attachment. Partial sequences, which may be advantageously used in the context of the present invention, for example, in antisense orientation, are for example nucleic acids having a sequence shown in SEQ ID NO: 5, 6 or 7. These partial sequences are segments of the nucleic acid according to SEQ ID NO: 3. However, any other nucleic acids with sequences or partial sequences of SEQ ID 1-3 can be used, for example, in the antisense direction.

The partial sequence preferably comprises a nucleic acid with at least 15, preferably at least 20, 25, 30, 35, 40, 45, 50, 60, 70, 80, 90, or at least 100 consecutive nucleotides, more preferably at least 150, 200, 250, 300, 350, 400 or 450 consecutive nucleotides. A portion of a protein (see, e.g., letter f) above) preferably comprises at least 5, preferably at least 10, 15, 20, 25, 30, 40 or 50, more preferably at least 60, 70, 80, 90, or at least 100 consecutive amino acids of SEQ ID NO: 4. The sequence portion of SEQ ID NO: 4 (see, e.g., letter g) above) preferably comprises at least 50, 60, 70, 80 or 90, more preferably at least 100, 120, 150, 200 or 250 consecutive amino acids of SEQ ID NO: 4. The necessary or useful length of the partial sequence of the nucleic acid or protein or the sequence section can be selected by the person of ordinary skill in the art with the aid of his general technical skills and, where appropriate, by carrying out routine tests of the approach and the intended effect, without this requiring an inventive step.

The nucleic acid is preferably at least 85%, preferably at least 90%, 95%, 96%, 97%, 98% or 99%, more preferably at least 99.5%, 99.6%, 99.7%, 99.8% or 99.9% identical to a sequence or partial sequence of SEQ ID NO: 1-3.

In a further aspect, the present invention concerns the use of one or more of the inventive nucleic acids for inhibition of bolting and flowering of sugar beet plant. As already indicated above, a nucleic acid can be introduced into a sugar beet plant, for example, in antisense orientation, thereby causing an inhibition of the genes responsible for bolting and flowering. Methods which are suitable for introducing a nucleic acid of the present invention in a sugar beet cell are known to the skilled person, and include for example the *Agrobacterium*-mediated transformation. The introduction of a nucleic acid in antisense orientation into a plant is only one of the known processes for the inhibition or suppression of gene activity. The inventive nucleic acids can also be used advantageously also in the context of other procedures or mechanisms that can cause an inhibition or suppression of bolting/flowering.

Furthermore, the inventive nucleic acids are also used as a probe to identify other factors, genes or gene products, with the help of the flowering and bolting of sugar beet plants can be inhibited and/or suppressed.

In a further aspect the present invention concerns a protein having an amino acid sequence of SEQ ID NO: 4 or a protein having an amino acid sequence that comprises a sequence segment of SEQ ID NO: 4, preferably at least 50, 60, 70, 80 or 90, preferably at least 100, 120, 150, 200, or at least 250 consecutive amino acids of SEQ ID NO: 4, or a protein from *Beta vulgaris* homologous to a protein with the amino acid sequence or a sequence segment of SEQ ID NO: 4. The protein or any part thereof, or the corresponding amino acid sequences may/could for example be used as a probe at the amino acid level to identify other factors, genes or gene products which can be used to inhibit and/or suppress the flowering and bolting of sugar beet plants.

In yet a further aspect the present invention relates to a method for producing a transgenic sugar beet plant comprising the steps of (a) transforming a sugar beet cell with one or more nucleic acids of the present invention and (b) regenerating a sugar beet plant from the transformed sugar beet cell. The transformation of sugar beet cell can occur, for example, using known vectors, e.g. a Ti-plasmid, and is known to the skilled person. The inventive nucleic acids may be controlled advantageously by a suitable promoter in such a vector.

The invention also relates to a vector or a mobile genetic element that includes one or more inventive nucleic acids. Vectors and mobile genetic elements are known in the art and include, for example, plasmids such as the Ti-plasmid. The vector or mobile genetic element can advantageously contain control elements, e.g. a promoter.

Furthermore, the invention relates to a sugar beet plant comprising one or more inventive nucleic acids, preferably under the control of a suitable promoter, and which is inhibited in bolting and flowering, as well as seeds and/or parts of a sugar beet plant of the present invention transformed with one or more inventive nucleic acids.

The invention is described below with reference to exemplary embodiments and the accompanying figures purely for illustrative purposes.

EMBODIMENTS

Identification/Isolation of a Complete cDNA of Beet for Suppressing of Bolting and Flowering Analysis by a specially created proprietary sugar beet EST database, a 1499 bp long, incomplete cDNA (SEQ ID NO: 3) was identified. Based on this incomplete cDNA clone bank, this sequence has been completed. The resulting sequence of the c-DNA (SEQ ID NO: 2) consisted of 1962 bp (2285 bp including 3'UTR). The protein resulting therefrom comprises 653 amino acids (SEQ ID NO: 4). The corresponding genomic DNA sequence (SEQ ID NO: 1) comprises 2366 bp.

Figure 13:
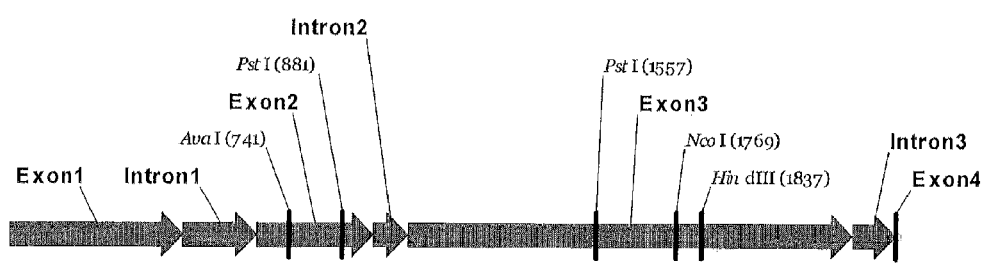
Figure 14:
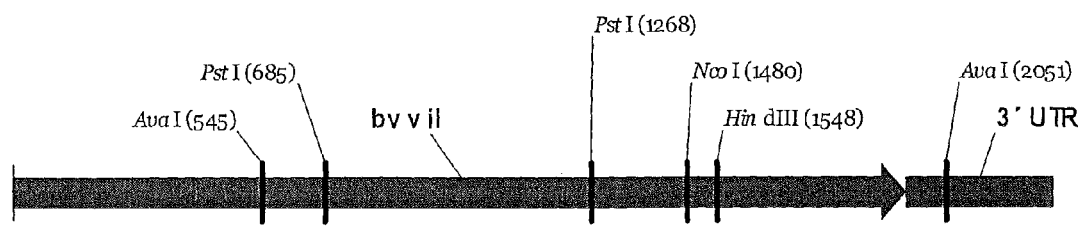
FIG. 14 Structure of the BvVIL cDNA sequence

An alignment of genomic DNA with cDNA shows the structure of the total DNA, which consists of four exons and three introns (FIG. 13). A schematic representation of the cDNA is found in FIG. 14.

Characterization/Annotation of the Sequence

A comparison (BLAST''') of the resulting full-length clone and the translated protein sequence shows only low level of sequence similarity with *Arabidopsis* "flowering genes" (e.g. AtVIL- and AtVIN-family). These include the genes VIN3 (VRN7), VIL1 (VRN5), VIL2 (VEL1), VIL3 (VEL2) and VIL4 (VEL3). The highest similarity over the entire sequence length is to AtVIL1 at 57.2% (see Table 1).

TABLE 1

Sequence comparison of Bv-VIL with *Arabidopsis thaliana* (At)-VIL-candidates at the DNA level. The comparison was with At-VIN3 over a length of 2343 bp, with At-VIL1 over a length of 2163 bp, with At-VIL2 over a length of 2555 bp, with At-VIL3 over a length of 1700 bp, and with At-VIL4 over a length of 1251 bp using the program AlignX (ClustalW).

|  | AtVIN3 | AtVIL1 | AtVIL2 | AtVIL3 | AtVIL4 |
|---|---|---|---|---|---|
| BvVIL | 46.0% | 57.2% | 51.5% | 49.8% | 45.9% |

A comparison of the sequences at the protein level with the AtVIL- and -VIN-gene family, both over the entire sequence as well as focusing on the different domains (characteristic for the VIL and VIN-gene family are the PHD, the FNIII and the VID domains) and the areas between the domains also shows a low homology (see Table 2).

TABLE 2

BvVIL sequence at the protein level compared with VIL genes from *Arabidopsis* (comparison with the overall sequences and individual domains).

| | Total | | | Pre-PHD | | PHD-Domains | | Inter-PHD-FN3 | | FN3 | | Inter-FN3-VID | | | VID | |
|---|---|---|---|---|---|---|---|---|---|---|---|---|---|---|---|---|
| | ident. % | pos. % | Cons.-L. AA | ident. % | pos. % | ident. % | pos. % | ident. % | pos. % | ident. % | pos. % | ident. % | pos. % | Com | ident. % | pos. % |
| AtVIL1 | 46.1 | 57.3 | 641 | 28.8 | 48.5 | 66.7 | 78.8 | 58.9 | 67.9 | 44.7 | 62.4 | 34.9 | 41.3 | | 49.6 | 61.7 |
| AtVIL2 | 30.9 | 42.8 | 688 | 34.7 | 43.2 | 50.8 | 62.3 | 39.4 | 53.8 | 24.7 | 43.5 | 13 | 21.9 | | 41.6 | 58.4 |
| AtVIL3 | 23.4 | 33.6 | 692 | 16.4 | 25.9 | 55.2 | 65.7 | 36.3 | 46 | 20.7 | 42.5 | 3.6 | 8.3 | gaps | 44 | 55 |
| AtVIN3 | 28.6 | 39.2 | 696 | 27.6 | 30.1 | 50 | 62.1 | 46.4 | 67.9 | 21.2 | 40 | 11.9 | 18 | gaps | 40.2 | 54.9 |

Figure 1:
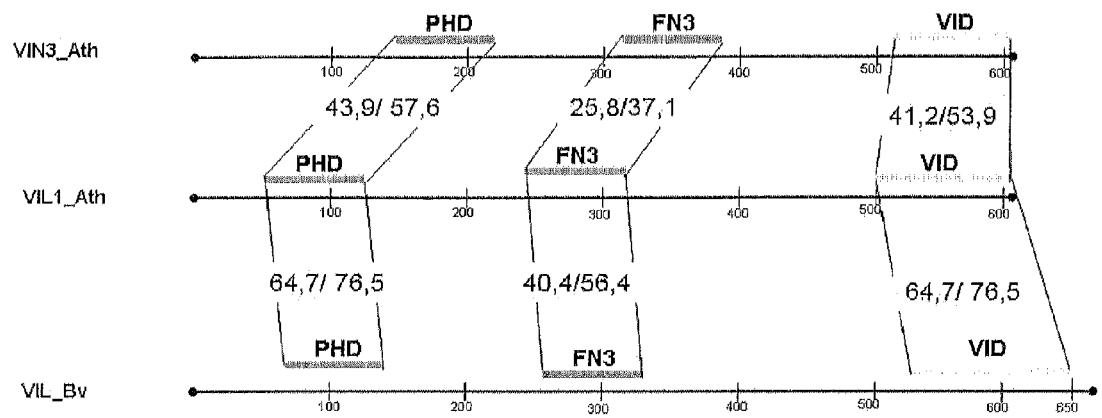
FIG. 1 Schematic comparison (BLAST™) of the respective position of the PHD, FNIII and VID domains in BvVIL, AtVIL1 and AtVIN3. Also indicated is the percentage of identical or similar nucleotides ("identities"/"positives", in %). VIN3_Ath=AtVIN3, VIL1_Ath=AtVIL1, VIL_By=BvVIL.

At = *Arabidopsis thaliana*, Bv = *Beta vulgaris*, Com = comment, AA = amino acids, ident = identical ("identities"), pos. = similar ("positives"), Cons.-L. AS = AS consensus length, gaps = gaps A comparison (BLAST™) of the individual domains shows that the new sequence is a VIL-like sequence. (FIG. 1). The sequence (SEQ ID NO: 1) is therefore referred to here as BvVIL (*Beta vulgaris* vernalization vin3-like).

A sequence comparison of BvVIL with AtVIL candidates for total DNA level shows only a maximum of 57.2% homology with AtVIL1. With other genes of the VIL-family, there is even lower sequence similarity.

An analysis of nontransgenic sugar beet for transcription of BvVIL before, during and after vernalization showed that the gene is transcribed not only after vernalization, but was constitutively active even before, during and after vernalization. In contrast, for example, VIN3 is activated only after a prolonged vernalization.

Production of RNAi Constructs

For the production of RNAi constructs three areas within the SEQ ID NO: 3 were used:

Nucleotides 775-1077 (SEQ ID NO: 5)
Nucleotides 779-1197 (SEQ ID NO: 6)
Nucleotides 971-1446 (SEQ ID NO: 7)

The sequence according to SEQ ID NO: 5 was amplified by PCR using the primer pairs F_PLT3~1:775U27, CTgggATACTTgggTgTTggAAAAAgC (SEQ ID NO: 8) and F_PLT3~1:1050 L28, TAgAAACATTggCgAgCCATTCATTAgC (SEQ ID NO: 9).

The sequence according to SEQ ID NO: 6 was amplified by PCR using the primer pair F_PLT3~1:779U24, gATACTTgggTgTTggAAAAAgCA (SEQ ID NO: 10) and F_PLT3~1:1175 L23, AATCAgTCATTggTgTggggATA (SEQ ID NO: 11).

The sequence according to SEQ ID NO: 7 was amplified by PCR using the primer pair F_PLT3~1:971U21, CAAgATggCCAgAggTATTgT (SEQ ID NO: 12) and F_PLT3~1:1426 L21, CTTCCTTTTTACAgCCCACTg (SEQ ID NO: 13).

The PCR was performed using 10 ng of genomic sugar beet DNA, a primer concentration of 0.2 µM at an "annealing" temperature of 55° C. in a Multicycler PTC-200 (MJ Research, Watertown, USA). The PCR products were each integrated in the vector pRTRNAi (Hirner A, Ladwig F, Stransky H, Okumoto S, Keinath M, Harms A, Frommer W B, Koch W. (2006) *Arabidopsis* LHT1 is a High-Affinity Transporter for Cellular Amino Acid Uptake in Both Root Epidermis and Leaf Mesophyll, Plant Cell. 18 (8):1931-46) in an inverted-repeat structure. The vector is based on the plasmid pRT100 and is designed for the production of "intronspliced" hairpin structures. The vector contains the 35S promoter for constitutive expression (Odell, J T, Nagy, F., and Chua, N.-H. (1985) Identification of DNA sequences required for activity of the cauliflower mosaic virus $^{35}$S promoter, Nature 313, 810-812), the ATAAP6 intron from *Arabidopsis* and one polyA terminator. The ATAAP6 intron is flanked by the cleavage sites XhoI/Ecl 13611 at the 5' end or by the restriction cleavage sites SmaI/SalI at the 3'-end, respectively. This enables the integration of identical fragments in a "sense" and "antisense", if these fragments have the compatible restriction sites XhoI or SalI, or are stumped on the other end ("blunt end"). For this the original PCR products were reamplified with new PCR primers extended by these restriction sites: Sal-SMA-775>1077 gagaggacgtcgacctgggatacttgggtg (SEQ ID NO: 14) and cccccgggtagaaacattggcgagc (SEQ ID NO: 15), SAL-SMA-779>1197 gagaggacgtcgacgatacttgggtgttgg (SEQ ID NO: 16) and cccccgggaatcagtcattggtgtgggata (SEQ ID NO: 17), XHO-SMA-971>1446 gagaggacctcgagcaagatggccagaggt (SEQ ID NO: 18) and gtcgaccccccccgggct-tccttttt (SEQ ID NO: 19). For further use the PCR fragments was cloned in the TA cloning vector pCR2.1 (TOPO TA Cloning Kit (Invitrogen, Carlsbad, USA)) and transformed in *E. coli*. A blue-white selection enabled the identification of recombinant plasmids (Sambrook, J., Fritsch, E. F., and Maniatis, T, 1989, in Molecular Cloning, A Laboratory Manual, Cold Spring Harbor Laboratory Press, New York). In the white colonies the expression of ss-galactosidase is suppressed by an insert, which results in white colonies, because the enzyme substrate added to the medium is no longer cleaved. A subsequent sequencing with M13-fwd/rev-Primern was performed at Eurofins MWG Operon (Ebersberg, Germany). The analysis and the alignment of the sequence data was performed using the program Vector NTI (Invitrogen, Carlsbad, USA).

Figure 4:
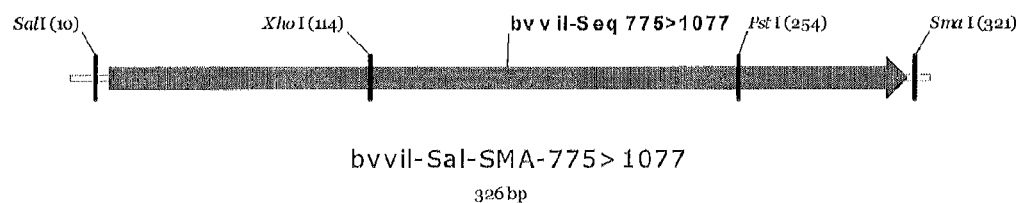
FIGS. 4-6 Schematic representation of the fragments Sal-SMA-775>1077 (FIG. 4), Sal-SMA-779>1197 (FIG. 5) and Sal-SMA-971>1466 (FIG. 6) used in the production of pRNAi vector FIGS. 7-9 Schematic representation of constructs pRNAi bvvil-775→1077sas (FIG. 7), pRNAi bvvil-779→1197sas (FIG. 8) and pRNAi bvvil-971→1466sas (FIG. 9) used for the production of RNAi vectors FIG. 10-12 Schematic representation of the binary Ti-plasmid-pLHRNAi bvvil-775-1077sas (FIG. 10), pLHRNAi-bvvil-779-1197sas (FIG. 11) and pLHRNAi-bvvil_971-1446sas (FIG. 12) used in *Agrobacterium*-mediated transformation FIG. 13 Schematic representation of the intron-exon structure of the genomic DNA of BvVIL, with indication of restriction sites.
Figure 5:
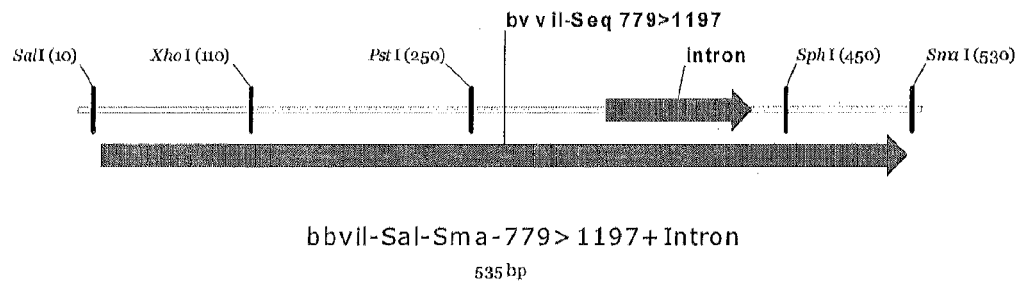
Figure 6:
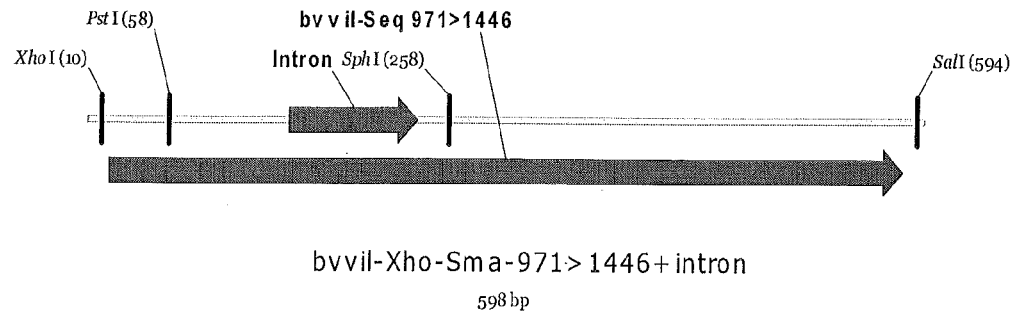
Figure 7:
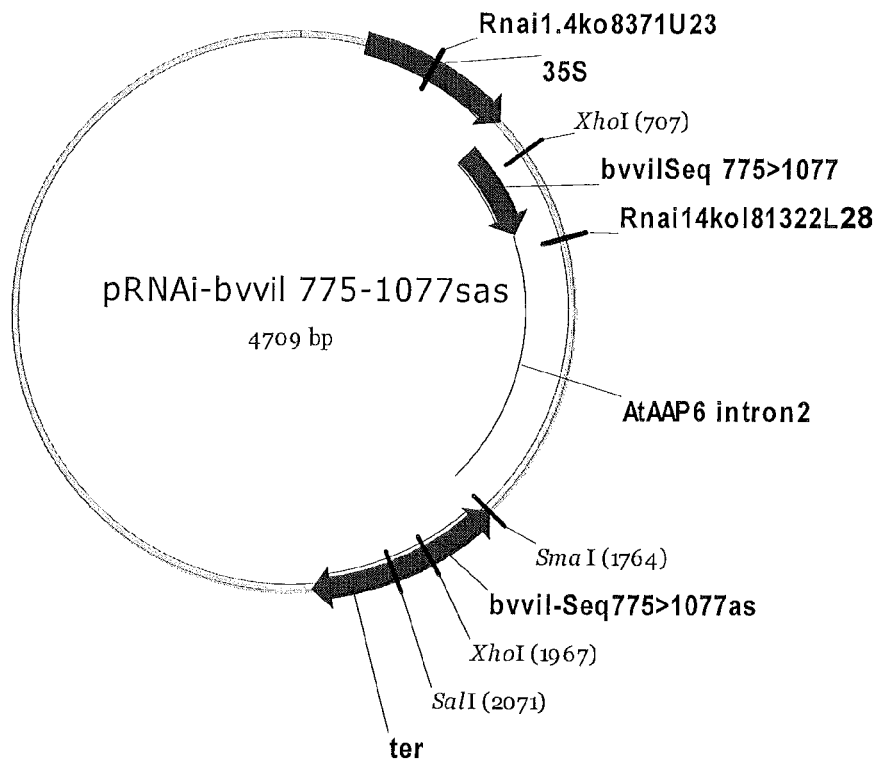
Figure 8:
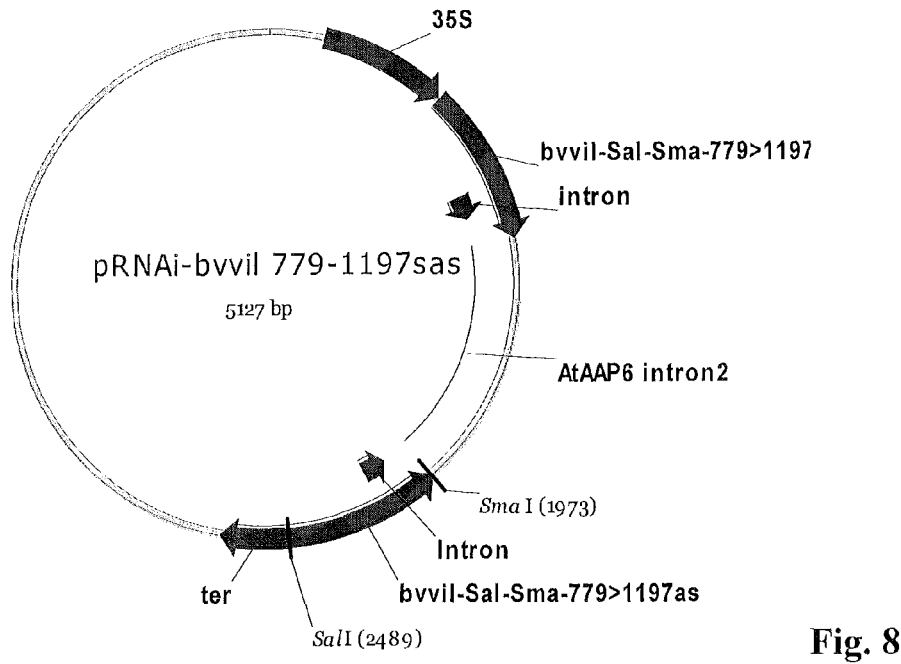
Figure 9:
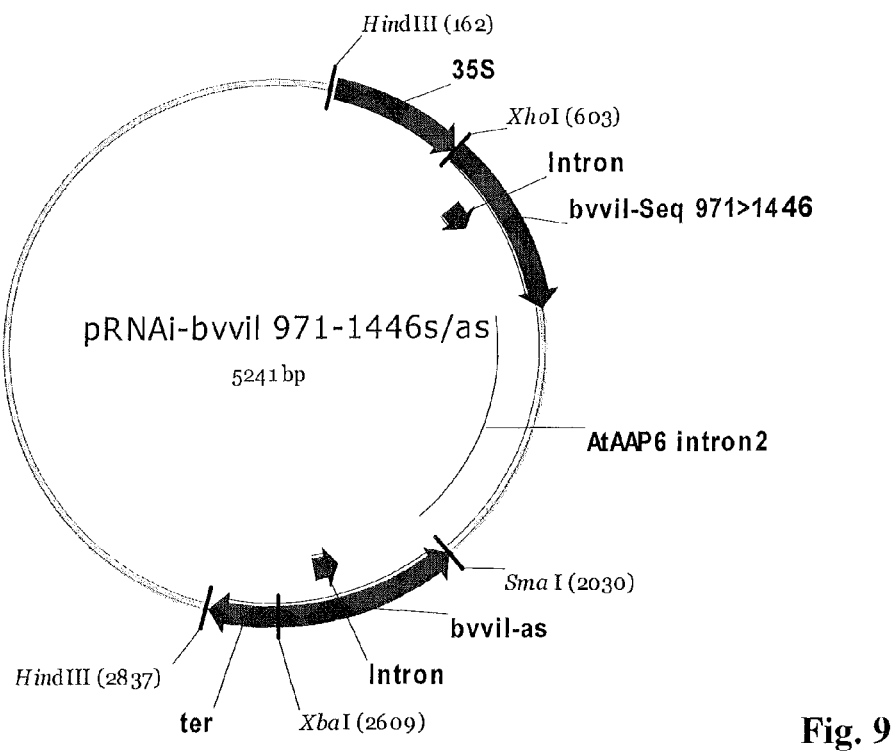
Figure 10:
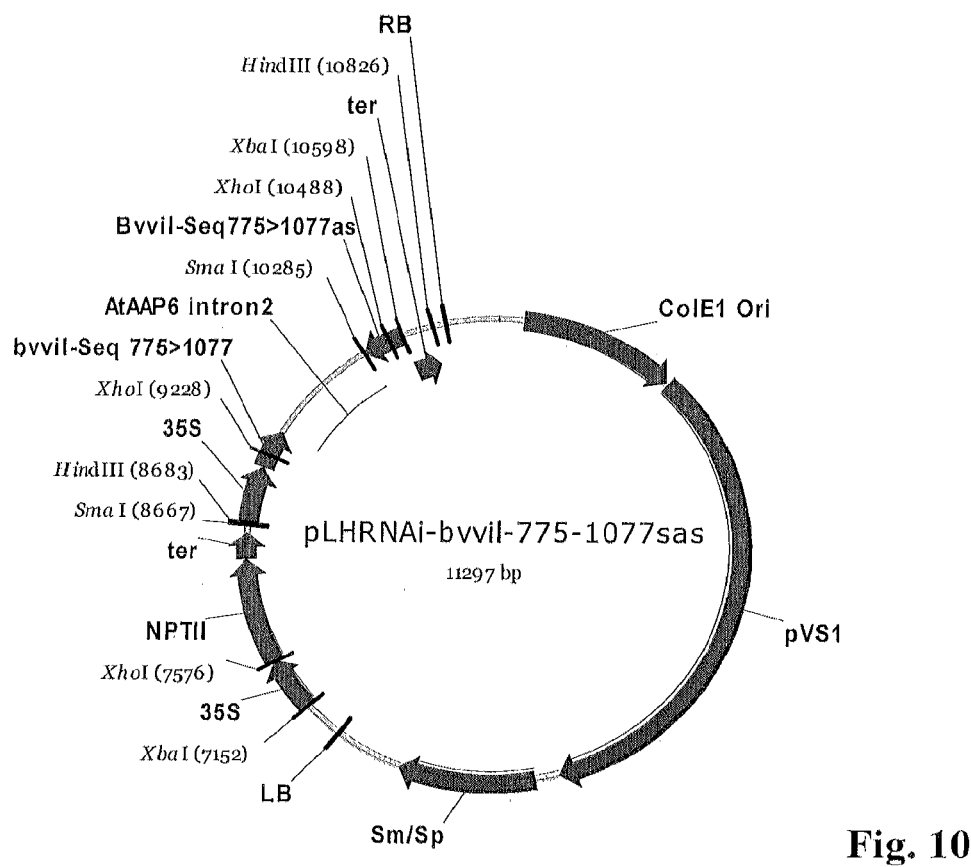
Figure 11:
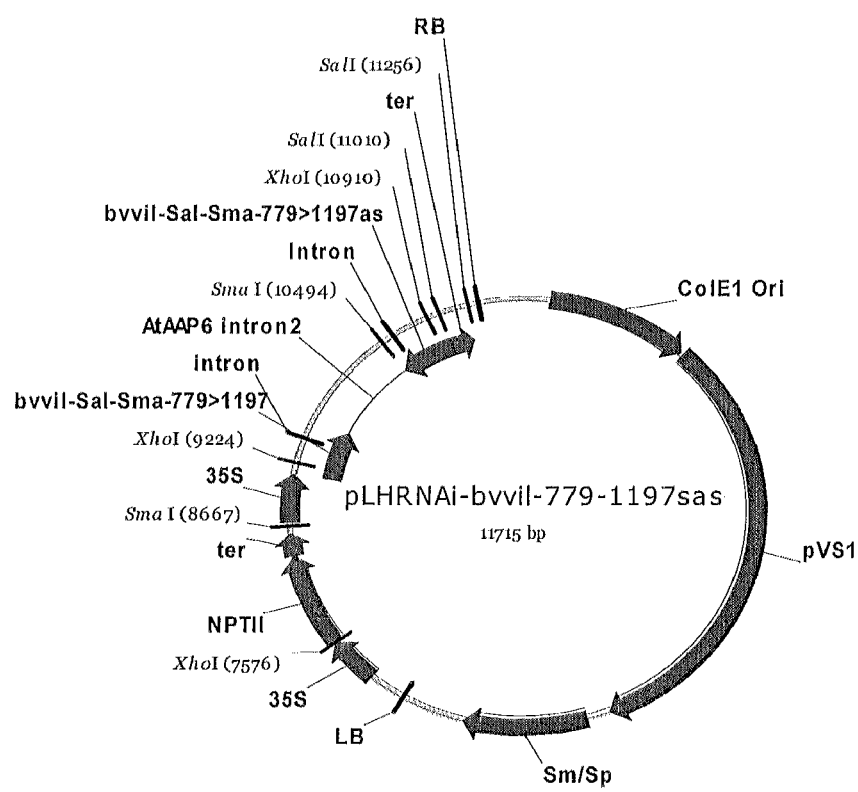
Figure 12:
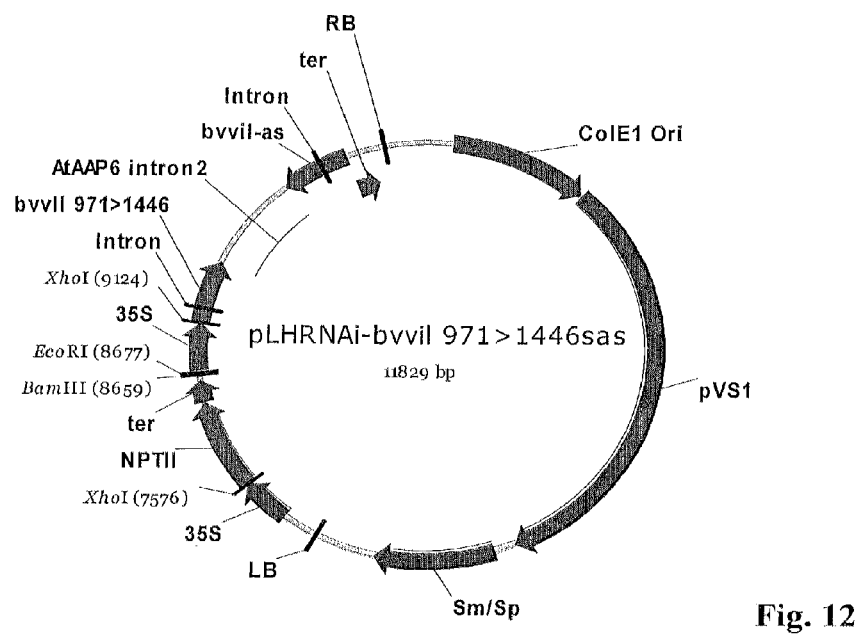

The fragments Sal-SMA-775>1077, SAL-SMA-779>1197 and XHO-SMA-971>1446 (FIGS. 4-6) were each cut from the Topovector by SalI/SmaI or XhoI/SmaI and then subsequently first ligated "in sense" with the SalI/SmaI or XhoI/Ecl 13611 cut pRTRNAi vector. Subsequently, the same fragments were religated for a second time in "antisense" in the compatible XhoI/Ecl 13611 or SalI/SmaI. The cloning procedures resulted in the vectors pRNAi-bvvil-775-1077sas, pRNAi-bvvil-779-1197sas and pRNAi-bvvil_971 1446sas (FIGS. 3, 7-9).

Production of Transformation Constructs

For the preparation of transformation constructs the binary transformation vector pLH9000 (Hausmann, L. and Toepfer, R. (1999) Entwicklung von Plasmid-Vektoren. Vortrage zur Pflanzenzüchtung: Bioengineering für Rapssorten nach Maβ 45: 155-172) (NCBI-Access number: AF458478) was used. After restriction of the pRNAi plasmids with HindIII the expression cassettes were isolated, cloned into the binary vector pLH9000, and the resulting plasmids were named pLHRNAi-bvvil-775-1077sas, pLHRNAi-bvvil-779-1197sas and pLHRNAi-bvvil-971-1446sas.

Sugar Beet Transformation and Checking of Transgenicity

For plant transformation the binary vectors pLHRNAi-bvvil-775-1077sas, pLHRNAi-bvvil-779-1197sas and pLHRNAi-bvvil-971-1446sas were used. The binary vectors were transformed in *Agrobacterium tumefaciens* strain C58C1 with the resident plasmid pGV3101 by a direct DNA transformation method (An, G. (1987), Binary Ti vectors for plant transformation and promoter analysis, Methods Enzymol. 153, 292-305). The selection of recombinant *A. tumefaciens* clones was performed using the antibiotic streptomycin (50 mg/l). The transformation of sugar beet was carried out according to Lindsey et al. (1991) using the antibiotic kanamycin (Lindsey, K., Gallois, P., Eady, C. (1991), Regeneration and transformation of sugar beet by *Agrobacterium tumefaciens*, Plant Tissue Culture Manual B7: 1-13, Kluwer Academic Publishers). The transgenicity the plants was verified by PCR. The use of primers GTGGAGAGGCTATTCGGTA (SEQ ID NO: 20) and CCACCATGATATTCGGCAAG (SEQ ID NO: 21) led to the amplification of a 553 bp DNA fragment from the nptII gene. The PCR was performed using 10 ng genomic DNA, a primer concentration of 0.2 µM at an annealing temperature of 55° C. in a Multicycler PTC-200 (MJ Research, Watertown, USA).

Checking of the Flowering and Bolting Behavior of the Transformants

Approximately 40 independent transformants together with nontransgenic isogenic controls were multiplied in vitro and transferred into the greenhouse. After an adjustment period, the transformants were subjected to vernalization for 3 months at 8° C. in a cooling chamber (winter simulation). Subsequently, the transformants, as well as identically treated non-transgenic control plants, were transferred back into the greenhouse (25° C.). Shortly after transfer, already after 10 days, the control plants began to bolt. After c. 4 weeks the control plants began to bloom. In contrast, 10 of the 40 transformants (25%), showed surprisingly no response on the induction of bolting and flowering by vernalization.

Figure 2:
FIG. 2 Bolting and flowering resistant sugar beet. Left: bolt-resistant transformant BvVIL WB4-7 (left in figure) compared with bolting control (pictured right); Right: BvVIL transformant WB4-7, several months old FIG. 3 Schematic representation of the structure of the used RNAi cassette.
Figure 3:

Non-bolting and non-flowering plants could be obtained from transformants of all three constructs. The position of the used sequence in the gene was not a factor for the function. The resulting transformants behaved like not-vernalized sugar beet. They neither start neither to bolt nor to bloom. For each independent transformant 30 plants were tested. All plants were without exception bolting and flowering resistant. None of the plants showed deviations from the normal phenotype. The plants were cultivated further, they continued to develop to normal beets with normal beet bodies. The bolting and flowering resistance was maintained throughout the test period of more than 4 months (FIG. 2).

Some of the plants were vernalized a second time for another three months. Even after this second vernalization, these plants after transfer back to the greenhouse at 25° C. could not be induced to bolt or flower.

Surprisingly, using the inventive transgenic approach, the vernalization or its effect, namely the bolting and flowering, completely blocked or reversed in sugar beet.

Evidence of Repression of BvVIL in Sugar Beet by RNAi Approach Using expression analysis of plants during and after vernalization.

From seven-week-old greenhouse-grown plants of sugar beet lines 3DC4156-wb5-1, 3DC4156-wb4-1, 3DC4156-wb4-14, 3DC4156-wb4-5, 3DC4156-wb5-18, 3DC4156-wb4-9, 3DC4156-wb4-7, 3DC4156-wb3-4, 3DC4156-wb3-4, 3DC4156-wb7-1, 3DC4156-wb18-1 and a non-transgenic 3DC4156, that were for the last three weeks in vernalization, RNA was isolated with TRI Reagent (Sigma, St. Louis, USA) according to manufacturer's protocol.

The RNA used for cDNA synthesis was checked for contamination with genomic DNA by PCR, while in parallel the result of the cDNA synthesis was investigated. Here, the DNA polymerase FIREPoI (Solis Biodyne, Tartu, Estonia) was used according to the manufacturer's instructions. As control, whole DNA was used. The PCR program was calculated for a fragment size of 369 bp. The primers were synthesized by Eurofins MWG Operon (Ebersberg, Germany) and are listed in Table 3.

TABLE 3

Primers for analysis of RNA/cDNA

| | |
|---|---|
| vin3fwd1994 | tgacctaaatgtagtttcagttcc (SEQ ID NO: 22) |
| vin3rev2317 | tcaaagttaccgtctagagaacc (SEQ ID NO: 23) |

Total DNA was isolated from four-week-old greenhouse-grown plants of the sugar beet line 3DC4156 with the DNeasy-Plant-Mini-Kit (Qiagen, Hilden, Germany) according to manufacturer's protocol. The RevertAid first-strand-cDNA-Synthes-kit from Fermentas (Vilnius, Lithuania) was used for synthesis of cDNA, wherein the manufacturer's instructions were followed.

The cDNA was used as a 1:10 dilution for qPCR analysis with an ABI StepOnePlus Real-time PCR machine, a SYBR green-based qPCR was performed. The POWER SYBR green PCR mix from ABI (Foster City, USA) was used as reaction buffer. During preparation of the reaction preparation the manufacturer's instructions were followed, respectively three repetitions were carried out. The primers for the qPCR were synthesized by Eurofins MWG Operon (Ebersberg, Germany) and are listed in Table 4. The primer pair nlosrealt1 and nlosrealt2 served to normalize it.

TABLE 4

Primers for qPCR analysis

| | |
|---|---|
| nlosrealt1 | GAGGAACTAGACATGGGGATACAT (SEQ ID NO: 24) |
| nlosrealt2 | GCGATACAAAGTAGACATTAGAACTC (SEQ ID NO: 25) |
| vin3realt1 | TAGGAAGCAAAGCAGGAAGGGA (SEQ ID NO: 26) |
| vin3realt2 | CCTCCGACAGAACGCATCATCT (SEQ ID NO: 27) |

QPCR was performed as shown in Table 5.

TABLE 5 qPCR/program

95° C. for 10 min
95° C. for 15 s
58° C. for 30 s
72° C. for 30 s
95° C. for 15 s
60° C. for 1 min
+0.5° C./s to 95° C. melting point determination Steps 2-4 were repeated 40 times, measurements were taken after step 4 and after every step of the melting point determination.

For the qPCR analysis, relative expression levels of BvVIL were determined. The expression level of the non/transgenic control was set as a 1. The results are shown in Table 6 for the plants of vernalization.

TABLE 6

Relative expression of BvVIL in vernalized wb-lines

| Line | Relative expression level |
|---|---|
| wb k 5121 | 0.154 |
| wb k 411 | 0.191 |
| wb k 4141 | 0.21 |
| wb k 451 | 0.238 |
| wb k 5181 | 0.269 |
| wb k 491 | 0.289 |
| wb k 472 | 0.384 |
| wb k 341 | 0.423 |
| wb k 716 | 0.529 |
| wb k 1811 | 0.673 |
| 3DC WT | 1 |

RNA was also isolated from several-month-old greenhouse-grown plants of sugar beet lines 3DC4156-wb5-1, 3DC4156-wb4-1, 3DC4156-wb4-14, 3DC4156-wb4-5, 3DC4156-wb5-18, 3DC4156-wb4-9, 3DC4156-wb4-7, 3DC4156-wb3-4, 3DC4156-wb3-4, 3DC4156-WB7-1, which remained non-bolting and non-flowering after several vernalizations, and a non-transgenic 3DC4156 that had been grown for four weeks at the greenhouse, with TRI-Reagent (Sigma, St. Louis, USA) according to manufacturer's protocol. For the cDNA synthesis, the same process as stated above for vernalized plants was used.

For the already several times vernalized yet non-bolting and non-flowering plants from the greenhouse, a qPCR analysis was performed following the same protocol. From this qPCR analysis also relative expression levels were determined for BvVIL. The expression level of non-transgenic control was set as a 1. The results for these plants are shown in Table 7.

TABLE 7

Relative expression of BvVIL in non-flowering and non-bolting wb lines

| Line | Relative expression level |
|---|---|
| wb k 5122 | 0.11 |
| wb k 4142 | 0.15 |
| wb k 5183 | 0.17 |
| wb k 496 | 0.21 |
| wb k 412 | 0.24 |
| wb k 451 | 0.24 |
| wb k 711 | 0.35 |
| wb k 471 | 0.36 |
| wb k 342 | 0.44 |
| 3DC WT | 1 |

In both experiments, a significant reduction of BvVIL transcript correlated with the tendency to bolting and flowering, and namely in such a way, that a reduction of BvVIL transcript to below 60% seems sufficient to a complete suppression of bolting and flowering.

An overview of the sequences listed in the application is included in Table 8 below:

TABLE 8

Sequence Overview

| SEQ ID NO: | Note |
|---|---|
| 1 | BvVIL, genomic DNA, 2366 nt |
| 2 | BvVIL, cDNA, including the 3'-UTR, 2285 (3'-UTR = nt 1963-2285) |
| 3 | BvVIL, incomplete cDNA, 1499 nt |
| 4 | BvVIL, protein sequence, 653 AA |
| 5 | nt 775-1077 of SEQ ID NO: 3, 303 nt |
| 6 | nt 779-1197 of SEQ ID NO: 3, 419 nt |
| 7 | nt 971-1446 of SEQ ID NO: 3, 476 nt |
| 8-27 | Primer |

Sequence Listing—Free Text

Primer

The term "artificial sequence" (english) in the sequence listing denotes "artificial sequence".

The invention claimed is:

1. An isolated nucleic acid for the inhibition of bolting and flowering of sugar beet plant, wherein the nucleic acid comprises a nucleotide sequence which
   a) comprises SEQ ID NO:5, 6 or 7 or at least 1183 consecutive nucleotides of SEQ ID NO: 2 or 3, or
   b) is complementary to SEQ ID NO:5, 6 or 7 or at least 1183 consecutive nucleotides of SEQ ID NO: 2 or 3, or
   c) comprises in the antisense direction SEQ ID NO:5, 6 or 7 or at least 1183 consecutive nucleotides of SEQ ID NO: 2 or 3 or a complementary sequence thereof, or
   d) comprises SEQ ID NO: 5, 6 or 7 and is at least 90% identical to a sequence selected from the group consisting of SEQ ID NO: 2-3, or comprises SEQ ID NO: 5, 6 or 7 and is at least 90% identical to a partial sequence of a sequence selected from the group consisting of SEQ ID NO: 2-3, or e) comprises SEQ ID NO: 5, 6 or 7 and encodes a protein with the amino acid sequence of SEQ ID NO: 4 or a part of the protein comprising at least 101 consecutive amino acids of SEQ ID NO: 4, or f) comprises SEQ ID NO: 5, 6 or 7 and encodes a protein with an amino acid sequence which is at least 90% identical to the sequence of SEQ ID NO: 4 or at least 90% identical to a sequence a sequence segment comprising at least 101 consecutive amino acids of SEQ ID NO: 4, or g) comprises SEQ ID NO: 5, 6 or 7 and hybridizes under stringent conditions with a sequence selected from the group consisting of SEQ ID NO: 2-3 or a nucleotide sequence complementary thereto or a nucleotide sequence oriented in the antisense direction thereto, wherein the stringent conditions include hybridization in 4×SSC at 65° C., followed by repeated washing in 0.1×SSC at 65° C. for a total of about 1 hour.

2. The nucleic acid according to claim 1, wherein the nucleic acid is at least 95% identical to a sequence or partial sequence of SEQ ID NO: 2-3.

3. A method for producing a transgenic sugar beet plant, where the bolting and flowering is inhibited after vernalization, comprising the steps of
(a) transforming a sugar beet cell with one or more nucleic acids according to claim 1 and (b) generating a sugar beet plant from the transformed sugar beet cell.

4. A vector or mobile genetic element, comprising one or more nucleic acids according to claim 1 and/or a nucleic acid for the inhibition of bolting and flowering of a sugar beet plant, wherein the nucleic acid comprises a nucleotide sequence which
a) is a partial sequence comprising at least 303 consecutive nucleotides of SEQ ID NO: 2 or 3, or b) is complementary to a partial sequence comprising at least 303 consecutive nucleotides of SEQ ID NO: 2 or 3, or exhibits in the antisense direction a partial sequence comprising at least 303 consecutive nucleotides of SEQ ID NO: 2 or 3 or a complementary sequence thereof.

5. A transgenic sugar beet plant in which bolting and flowering is inhibited, wherein the transgenic sugar beet plant comprises one or more nucleic acids according to claim 1 or the vector or mobile genetic element according to claim 4 as transgenes.

6. A seed or part of a transgenic sugar beet plant in which bolting and flowering is inhibited, which is transformed with one or more nucleic acids according to claim 1 or the vector or mobile genetic element according to claim 4 as transgenes.

7. A process for the inhibition of bolting and flowering of sugar beet plant comprising the steps of (a) introducing one or more nucleic acids according to claim 1 in a sugar beet cell, and (b) generating a sugar beet plant from the sugar beet cell, wherein the introduced one or more nucleic acids leads to a reduction of the protein transcript having an amino acid sequence of SEQ ID NO: 4 or of a thereto homologous protein from *Beta vulgaris* in the sugar beet plant.

8. The nucleic acid of claim 1, wherein the sequence comprising SEQ ID NO:5, 6 or 7 comprises at least 350 consecutive nucleotides of SEQ ID NO: 2 or 3, and/or the part of the protein comprises at least 101 consecutive amino acids of SEQ ID NO: 4, and/or the protein comprises at least 150 sequential amino acids of SEQ ID NO: 4.

9. The nucleic acid of claim 1, wherein the sequence sequence comprising SEQ ID NO:5, 6 or 7 comprises at least 450 consecutive nucleotides of SEQ ID NO: 2 or 3, and/or the the protein comprises at least 250 sequential amino acids of SEQ ID NO: 4.

10. The nucleic acid according to claim 1, wherein the nucleic acid is at least 97% identical to a sequence or partial sequence of SEQ ID NO: 2-3.

11. The nucleic acid according to claim 1, wherein the nucleic acid is at least 99.5% identical to a sequence or partial sequence of SEQ ID NO: 2-3.

12. The nucleic acid according to claim 1, wherein the nucleic acid is at least 99.6% identical to a sequence or partial sequence of SEQ ID NO: 2-3.

13. The nucleic acid according to claim 1, wherein the nucleic acid is at least 99.7% identical to a sequence or partial sequence of SEQ ID NO: 2-3.

14. The nucleic acid according to claim 1, wherein the nucleic acid is at least 99.8% identical to a sequence or partial sequence of SEQ ID NO: 2-3.

15. The nucleic acid according to claim 1, wherein the nucleic acid is at least 99.9% identical to a sequence or partial sequence of SEQ ID NO: 2-3.

* * * * *